United States Patent [19]

Real et al.

[11] Patent Number: 4,562,160

[45] Date of Patent: Dec. 31, 1985

[54] MELANOMA TUMOR ANTIGEN AND AUTOLOGOUS ANTIBODY

[75] Inventors: Francisco X. Real, New York; M. Jules Mattes, Jamaica Estates; Alan N. Houghton; Philip O. Livingston, both of New York; Kenneth O. Lloyd, Bronx, all of N.Y.; Herbert F. Oettgen, New Canaan, Conn.; Lloyd J. Old, New York, N.Y.

[73] Assignee: Sloan-Kettering Institute, New York, N.Y.

[21] Appl. No.: 482,153

[22] Filed: Apr. 1, 1983

[51] Int. Cl.$^4$ .................. G01N 33/54; A61K 39/395; A61K 39/44; A61K 43/00

[52] U.S. Cl. ................. 436/539; 260/112 R; 424/1.1; 424/85; 424/88; 435/4; 435/7; 435/948; 436/518; 436/536; 436/542; 436/543; 436/804; 436/813; 436/815; 436/823

[58] Field of Search ................ 436/518, 536–542, 436/543, 548, 804, 813, 815, 823; 435/7, 68, 70, 172.2, 240, 948, 4; 260/112 R; 935/95, 99–104, 106–110; 424/1.1, 85, 88

[56] References Cited

U.S. PATENT DOCUMENTS 4,172,124  10/1979  Koprowski et al. .................. 424/85
4,361,544  11/1982  Goldenberg ......................... 424/1.1

OTHER PUBLICATIONS

Loop, S. M. et al., Int. J. Cancer, vol. 27, pp. 775–781 (1981).
Natali, P. G. et al., J. National Cancer Institute, vol. 67(3), pp. 591–601 (1981).
Steplewski, Z. et al., Cancer Research, vol. 41, pp. 2723–2727 (1981).
Seeger, R. C. et al., Cancer Research, vol. 41, pp. 2714–2717 (1981).
Bumol, T. F. et al., Hybridoma, vol. 1, pp. 283–292 (1–1982).
Yeh, M. Y. et al., International J. of Cancer, vol. 29, pp. 269–275 (1982).
Houghton, A. N. et al., J. Experimental Medicine, vol. 156(6), pp. 1755–1766 (1982).
Reisfeld, R. A. et al., Nature, vol. 298, pp. 325–326 (1982).
Pukel C. S. et al., J. Experimental Medicine, vol. 155, pp. 1133–1147 (4–1982).

Johnson, J. P. et al., European J. Immunology, vol. 11, pp. 825–831 (1981).
Morgan, A. C. et al., Hybridoma, vol. 1, pp. 27–36 (1981).
Wilson, B. S. et al., Int. J. Cancer, vol. 28, pp. 293–300 (1981).
Brown, J. P. et al., Proc. Natl. Acad. Sci. USA, vol. 78, pp. 539–543 (1981).
Mitchell, K. F. et al., Proc. Natl. Acad. Sci. USA, vol. 77, pp. 7287–7291 (1980).
Dippold, W. G. et al., Proc. Natl. Acad. Sci. USA, vol. 77, pp. 6114–6118 (1980).
Carrel, S. et al., Cancer Research, vol. 40, pp. 2523–2528 (1980).
Brown, J. P. et al., J. Biological Chemistry, vol. 255(11), pp. 4980–4983 (1980).
Floyd, K. O. et al., J. National Cancer Institute, vol. 63(3), pp. 623–634 (1979).
Ueda, R. et al., J. Experimental Medicine, vol. 150, pp. 564–579 (1979).
Carey, T. E. et al., Proc. Natl. Acad. Sci., USA, vol. 76(6), pp. 2898–2902 (1979).
Pfreundschuh, M. et al., Proc. Natl. Acad. Sci., USA, vol. 75(10), pp. 5122–5126 (1978).
Koprowski, H. et al., Proc. Natl. Acad. Sci. USA, vol. 75(7), pp. 3405–3409 (1978).

Primary Examiner—Thomas G. Wiseman
Assistant Examiner—M. Moskowitz
Attorney, Agent, or Firm—Felfe & Lynch

[57] ABSTRACT

The present invention concerns novel immunoprecipitating autologous antibodies which recognize the Class 1 gp90 antigen on melanoma cells. These antibodies, optionally tagged with a chromophoric or radioactive label and immobilized on an inert support, may be used to recognize and isolate the gp90 antigen from melanoma cell extracts. Monoclonal antibodies to melanoma may be screened with the gp90 antigen for those which recognize epitopes other than the FD antigenic system.

The cell line containing the gp90 antigen which has been cultured in vitro is a source of gp90 antigen for generation of monoclonal antibodies which will be useful in analyzing the gp90 antigen for those epitopes which may be of diagnostic value in immunoassay of melanoma.

9 Claims, No Drawings

MELANOMA TUMOR ANTIGEN AND AUTOLOGOUS ANTIBODY

This invention concerns the 90 gp antigen on melanoma cells and the autologous antibodies which recognize the FD determinant on this antigen

BACKGROUND

The main questions in human tumor immunology continue to be whether tumor cells express cell surface antigens absent from all normal cell types and whether the immune system is able to recognize these new antigens and mount an immune response against them.

To answer these questions, the serological response of cancer patients against their tumor cells has been studied by autologous typing, where the patients' sera are tested on the autologous cultured tumor cell line and absorption tests are done to determine the specificity of the reactivity. Autologous typing has been used to study the sera of patients with melanoma, astrocytoma, renal cancer and leukemia. The antigens recognized by the patients' sera can be grouped in three different categories. Class 1 antigens or unique antigens only expressed by the autologous tumor cell line; Class 2 antigens expressed by the autologus tumor and other allogeneic tumor or normal cells of the same type or related embryologic origin (Class 2 antigens turn out to be differentiation antigens); Class 3 antigens widely distributed and found in the autologus tumor and also in allogeneic tumor cell lines and normal cells of varied embryologic origin.

Although all three classes of antigens are of interest because of the ability to be autoimmunogenic, Class 1 antigens are particularly interesting because of their very restricted distribution.

The characterization of the unique antigens has been hampered by the small number of patients who develop these antibodies, the low titer of the sera and the inability to immunoprecipitate the antigen from cultured cells.

SUMMARY

The present invention concerns novel immunoprecipitating autologous antibodies which recognize the Class 1 gp90 antigen on melanoma cells. These antibodies, optionally tagged with a chromophoric or radioactive label and immobilized on an inert support, may be used to recognize and isolate the gp90 antigen from melanoma cell extracts. Monoclonal antibodies to melanoma may be screened with the gp90 antigen for those which recognize epitopes other than the FD antigenic system.

The cell line containing the gp90 antigen which has been cultured in vitro is a source of gp90 antigen for generation of monoclonal antibodies which will be useful in analyzing the gp90 antigen for those epitopes which may be of diagnostic value in immunoassay of melanoma.

ISOLATION OF FD ANTIGEN

Tissue Culture

Tumor cell lines were used. The human fetal fibroblast cell line Flow 5000 was purchased from Flow Laboratories (Rockville, MD). B cell lines were established from peripheral blood lymphocytes from melanoma patients transformed by Epstein-Barr virus released from the B-95-8 marmoset lymphoid line.

Cultured cells were maintained in Eagle's non-essential medium supplemented with 2 mM glutamine, 1% nonessential aminoacids, 100 U/ml penicillin, 100 g/ml streptomycin, and 7.5% fetal bovine serum (FBS). To remove heterologous FBS components melanoma cells were grown for at least four subcultures in 10% human sera selected from AB blood type donors. The SK-MEL-131 melanoma cell line was also cultured in serum-free medium containing insulin (5 g/ml), transferrin (5 g/ml) and selenium (5 g/ml) (ITS medium, Collaborative Research Labs., Waltham, MA). Cultures were regularly tested for mycoplasma, fungi and bacteria and contaminated cultures were discarded.

Serological test

The protein A hemadsorption (PA) and immune adherence assays (IA) were done by methods well known in the art. Assays were performed in Falcon 3040 microtest II plates. Target cells were plated 1–3 days before the assay and incubated with human sera for one hour at room temperature. After washing with 5% IgG-free FBS (GGF-FBS) (Gibco, Grand Island, NY) phosphate buffered saline (PBS), indicator cells were added and incubated with the target cells for one hour at room temperature. The plates were then washed three times with 5% GGF-FBS-PBS and reactions were evaluated under a light microscope. When cells grown in human serum were tested, 2% human serum albumin in PBS was substituted for the 5% GGF-FBS-PBS. Qualitative absorptions were performed by absorbing 30 1 of a dilution of serum four fold more concentrated than the endpoint with a 30 1 pellet of packed cells for 30 min at room temperature and 30' at 40° C. Testing of residual antibody activity was done as for direct tests. To test for heat stability the cells were incubated for 5 min. in boiling water before absorption. Neuraminidase sensitivity was determined by incubating the target cells with Dulbecco's-PBS (Gibco, Grand Island, NY) containing neuraminidase (Calbiochem-Behring, La Jolla, CA) at a concentration of 50 U/ml at 37° C. for one hour prior to the serological assay. To detect shed antigen in spent culture medium, medium from SK-MEL-131 cells and from normal fibroblasts was collected, ultracentrifuged at 28,000 rpm for 30 min and used as diluent for FD serum. AFter 30 min at room temperature these dilutions were tested on SK-MEL-131 target cells.

Trypsin (Gibco, Grand Island, NY) treatment was at 0.5 mg/ml for 10 min at 37° C. Trypsinized target cells were tested for expression of the unique antigen after incubation for 0.5 and 6 hr. in medium containing (1) no additive, (2) cycloheximide (Sigma, St. Louis, MO) at a concentration of 10 g/ml or (3) monensin (Sigma, St. Louis, MO) at a concentration of 10 g/ml.

Immunoprecipitation of FD Antigen

The methods of metabolic incorporation of [$^3$H]mannose, and [$^{35}$S]methionine and solubilization of labeled cells are known in the art. Membrane preparations were solubilized with NP-40 (Calbiochem-Behring, La Jolla, CA) and $^{125}$I-labeled with chloramine T (Eastman, Rochester, NY). Culture medium from cells grown in ITS medium was concentrated ten times by pressure dialysis using an Amicon membrane with a 10,000 dalton exclusion limit than dialyzed for 72 hours against PBS. Iodination was done as described except that the column buffer was 50 mM Tris pH 7.5, 2% BSA, 10 mM NaI, 0.10M NaCl. Seven μl of human serum was incubated with the antigen overnight at 4° C. Precipitated molecules were extracted from pelleted *Staphylococcus aureus* (Enzyme Center, Boston, MA) with 60 μl 0.01M Tris HCl pH 7.2, 2.0% SDS, 12.0 mg/ml dithiothreitol (DTT), 15% (wgt/vol) sucrose, 0.01 pyronin Y by heating 5 minutes at 100° C., and analyzed by polyacrylamide gel electrophoresis (PAGE) using 9% gels. For 2-dimensional electrophoresis (isoelectric focusing followed by SDS-electrophoresis) immune precipitates were extracted and handled. For unreduced samples, DTT was omitted and 14.0 mg/ml iodoacetamide was added to samples. For absorption tests 30 μl of a 1:2 dilution of serum were absorbed with a 30 μl pellet for 30 min at room temperature, then for 30 min at 4° and the supernatant used for immunoprecipitation.

Lectin column fractionation

Beads conjugated with Concancavalin A, wheat germ agglutinin, lentil lectin and *Helix pomatia* lectin were purchased from Pharmacia (Piscataway, NJ) and beads conjugated with peanut agglutinin, soybean agglutinin and lectins from *Ulex europaeus*-I, *Bandeira simplicifoli*-I, *Dolichos biflorus, Pisum sativum, Ricinus communis*-I, *Vicia villosa, Lotus tetragonolobus* and *Limulus polyhemus* were purchased from E-Y Laboratories (San Mateo, CA). Columns of 0.5 ml were equilibrated with the iodination column buffer and iodinated antigen preparations were passed through the column. The material specifically bound to the column was eluted with the appropriate sugar at a 1M concentration. 0.7 ml fractions were collected and counted. Fractions corresponding to the peak counts were pooled and used for immunoprecipitation.

DEAE fractionation

DEAE-Sepharose (Pharmacia, Piscataway, NJ) was equilibrated with column buffer. For separation of IgG from human serum, 0.01M phosphate buffer pH 8.0 was used. For fractionation of the iodinated spent medium, column buffer was 10 mM Tris HCl pH 8.0 and fractions were eluted with 100 mM, 200 mM, 400 mM and 800 mM NaCl in 10 mM Tris Hcl pH 8.0

Autologous typing with sera from patient FD

Sera from patient FD was tested for reactivity with cell surface antigens of the autologous SK-MEL-131 cell line. Autologous reactions were detected with the Protein A and anti-human immunoglobulin mixed hemadsorption assays. DEAE chromatogrpahy of the FD serum showed that the reactivity was present in the IgG fraction.

When the Sk-MEL-131 cells were cultured for four passages or more in medium containing 10% normal human sera, the reactivity was detected with a titer which was twofold lower than the titer on cells cultured in medium containing FCS.

Variation in expression of the FD antigen

When the same sample of serum from patient FD was tested with the SK-MEL-131 cell line over a period of several months, a decrease in the titer was observed. When the cells were tested at passage 7 two weeks after being thawed from liquid nitrogen, the titer was 1/1280. At passage 14, after eight weeks of culture the titer was 1/320. After 6 months of culture, the titer was 1/40. After 10 months of culture, the titer was 1/10. Expression of the unique antigen could still be detected consistently by absorption tests after one year of in vitro culture. The decay in antigen expression was related to time in culture and not to passage number was established by testing cells that had been subcultured 14 vs. 4 times over a period of six months.

Absorption analysis of the specificity of FD serum

The specificity of serum FD was analyzed by absorption tests. Only the SK-MEL-131 cell line absorbed the reactivity completely. The antibody was not absorbed by 33 allogeneic melanoma cell lines, 32 cell lines derived from other tumor types, 4 cultures of normal kidney epithelial cells, 2 cultures of skin fibroblasts, EBV transformed lymphocytes from 8 individuals, including patient FD, and 4 xenogeneic cell lines. To exclude the possibility that the FD antigen might be related to fetal calf serum, absorption tests were carried out with SK-MEL-131 cell line adapted to grow in serum-free medium (ITS medium). These cultures absorbed completely the reactivity of serum FD with SK-MEL-131 grown in FCS. Among the allogeneic melanoma cell lines used for absorption tests were five in which other unique tumor antigens have been detected in our laboratory.

Characteristics of the FD antigen

Absorption tests with SK-MEL-131 cells heated to 100° C. for 5 minutes showed that the unique FD antigen was destroyed. SK-MEL-131 cells treated with trypsin were unreactive with FD serum. The re-expression of the antigen was determined by rosetting assays with target cells in suspension 0.5 and 6 hr after trypsinization. FIG. 5 shows that antigen expression was strong at 12 hr and reached maximum level at 48–72 hr after trypsinization in confluent cultures. Cycloheximide and monensin inhibited the re-expression of the antigen. Neuraminidase treatment of adherent cells did not affect expression of the FD antigen but abolished the reactivity with the $R_{24}$ antibody, which reacts with $G_{D3}$, disyaloganglioside. Spent cultured medium from SK-MEL-131 cells and from a culture of normal fibroblasts were ultracentrifuged and used as diluent for FD serum which was subsequently tested on SK-MEL-131 cells. The spent medium from SK-MEL-131 cells inhibited the reactivity whereas the medium from normal fibroblasts did not. Spent medium concentrated 10 times by pressure dialysis had strong inhibitory activity.

Spent culture medium from SK-MEL-131 cells was diluted 1:2 with fresh medium and incubated for 5 days with cultures from three melanoma cell lines (SK-MEL-127, SK-MEL-26 and SK-MEL-41). These cell lines had previously been tested for expression of the FD antigen and shown to be negative. After 3 weeks of culture in regular medium the cells were re-tested with FD serum. No reactivity with serum FD was detected.

Biochemical characterization of the FD antigen

FD serum immunoprecipitated a 90,000 dalton component from a radiolabeled preparation from SK-MEL-131 cells (FIG. 6). This component showed a pI of 5.5 in 2-dimensional gel electrophoresis. The reactivity of FD serum with the membrane preparation could be absorbed completely by the SK-MEL-131 cells but not by any of 14 other cell lines including melanomas, carcinomas and normal fibroblasts (Fig.). This reactivity was also not absorbed by autologous EBV-transformed lymphocytes.

This component was not seen by immunoprecipitation with cells metabolically labeled with [$^{35}$S]methionine or [$^3$H]glucosamine, but it was detected faintly with cells labeled with [$^3$H]mannose (data not shown).

Spent culture medium from SK-MEL-131 cells growing in serum-free medium was ultracentrifuged, concentrated 10-fold by pressure dialysis, labeled with $^{125}$I and used for immunoprecipitation. The 90,000 dalton component was detected. This antigen preparation was fractionated using 14 different lectin columns which are listed under methods, and the effluent and eluate from each column were tested by immunoprecipitation. The antigen was found in the effluent of all the lectin columns. In addition, the eluate of the Concanavalin A column contained a third of the precipitated antigen (FIG. 6). When the labeled cell membrane preparation was fractionated on a Concanavalin A column, the eluate contained essentially all of the precipitated antigen.

Immunodiagnostic potential of FD antigen

The FD antigens described herein are useful in the generation of monoclonal antibodies which will allow mapping of the antigen and identifying new epitopes. Those newly recognized epitopes which are shared with melanoma cells of other sources will be of diagnostic importance in tumors.

What is claimed:

1. Antibody purified from human serum which specifically binds to Class 1 FD gp 90 melanoma cell antigen.

2. Antibody of claim 1, immobilized on a solid support.

3. Antibody of claim 1 having a radioactive label.

4. A method of detecting the presence or lack of Class 1 FD gp 90 melanoma cell antigen comprising mixing a cell extract thought to contain said antigen with a human serum sample containing antibody which specifically binds to said antigen and incubating under conditions favoring formation of a complex of Class 1 FD gp 90 melanoma cells antigen and antibody specifically binding to said antigen, and determining whether or not a complex of said Class 1 FD gp 90 antigen and antibody specifically binding to said antigen has formed.

5. Method as in claim 4, wherein a complex of Class 1 FD gp 90 antigen and antibody specifically binding to said antigen is formed and is precipitated from said mixture.

6. A method of detecting the presence or lack thereof of monoclonal antibodies which specifically bind to epitopes of Class 1 FD gp 90 melanoma cell antigen comprising contacting a sample thought to contain said antibodies with a sample containing said antigen to form a mixture containing antibodies and antigen and incubating under conditions favoring formation of a complex between said antibodies and said antigen and determining whether or not a complex of said antibodies and said antigen has been formed.

7. A method of isolating Class 1 FD gp 90 melanoma cell antigen comprising mixing an extract of melanoma cells with a sample of human serum which contains antibody specifically binding to an epitope of said antigen and incubating the mixture under conditions favoring formation of a complex of said antigen and said antibody, precipitating the complex and isolating and separating the antigen and antibody of the precipitated complex.

8. A method as in claim 7, wherein the melanoma cells are taken from cell line SK-MEL-131.

9. Class 1 FD gp 90 melanoma cell antigen purified from human melanoma cells.

* * * * *